United States Patent [19]
Isse

[11] Patent Number: 5,681,262
[45] Date of Patent: Oct. 28, 1997

[54] ENDOSCOPE AND TOOL THEREFORE

[75] Inventor: Nicanor G. Isse, Pasadena, Calif.

[73] Assignee: Very Inventive Physicians Inc., Tucson, Ariz.

[21] Appl. No.: 480,413

[22] Filed: Jun. 7, 1995

Related U.S. Application Data

[63] Continuation-in-part of Ser. No. 318,196, Oct. 5, 1994, abandoned.

[51] Int. Cl.$^6$ ................................................ A61B 1/307
[52] U.S. Cl. .................... 600/127; 600/104; 600/121; 606/167; 606/45; 606/46
[58] Field of Search ............................... 606/67, 170, 172, 606/45–48; 600/113, 119, 121, 127, 129, 136, 104

[56] References Cited

U.S. PATENT DOCUMENTS

| | | | |
|---|---|---|---|
| 2,018,335 | 10/1935 | Wappler | 606/46 |
| 2,448,741 | 9/1948 | Scott et al. | 606/46 |
| 2,484,059 | 10/1949 | Wallace | 606/46 |
| 2,487,502 | 11/1949 | Willinsky | 606/46 |
| 2,583,937 | 1/1952 | Fossati | 606/46 |
| 4,473,076 | 9/1984 | Williams et al. | 606/172 |
| 5,133,713 | 7/1992 | Huang et al. | 606/46 |
| 5,151,401 | 9/1992 | Grossi et al. | 606/46 |
| 5,267,994 | 12/1993 | Gentelia et al. | 606/45 |
| 5,496,314 | 3/1996 | Eggers | 606/46 |
| 5,536,234 | 7/1996 | Newman | 600/104 |

*Primary Examiner*—Jennifer Bahr
*Assistant Examiner*—Rosiland Kearney
*Attorney, Agent, or Firm*—Mark Ogram

[57] ABSTRACT

An endoscope and tool therefore which provides a shroud for the protection of the viewing end of an endoscope. The shroud is curved and extends forward of and around the viewing end of an endoscope. This configuration vastly reducing tissue traumatization as tissue is "guided" about the smooth curved outer edges of the shroud. Therefore, the surgeon may use the shroud to separate tissue to improve the view through the endoscope without fear of injuring the patient. Further, even though the shroud extends around the viewing end of the endoscope, viewing remains unobscured as there is a cut-away section in the shroud through which the endoscope receives its image. Additionally, the shroud is capable of being equipped with surgical tools to assist in slicing, cauterizing, and biopsy removal, thereby permitting the surgeon to perform more activities and reducing the need for an assisting surgeon.

34 Claims, 4 Drawing Sheets

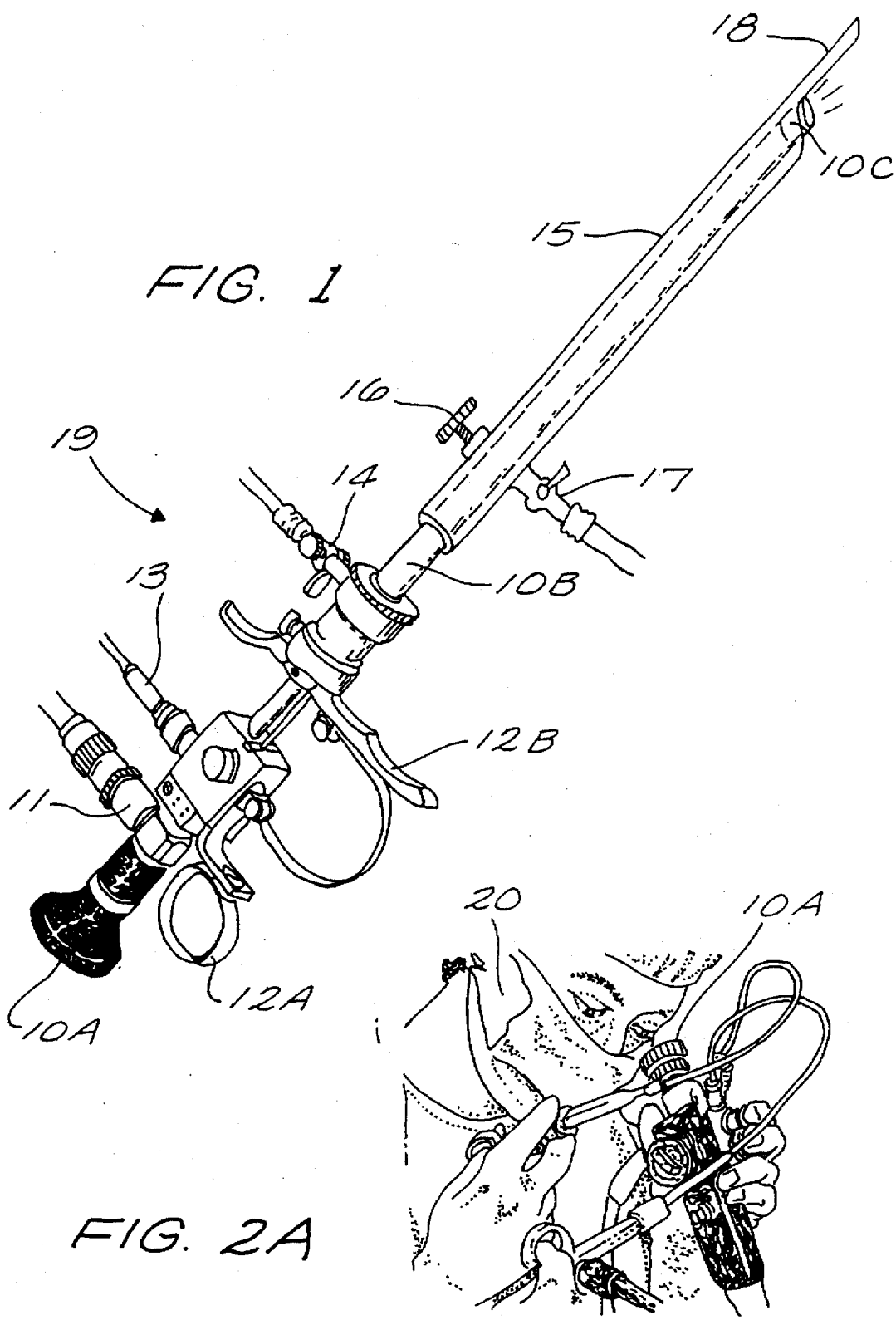

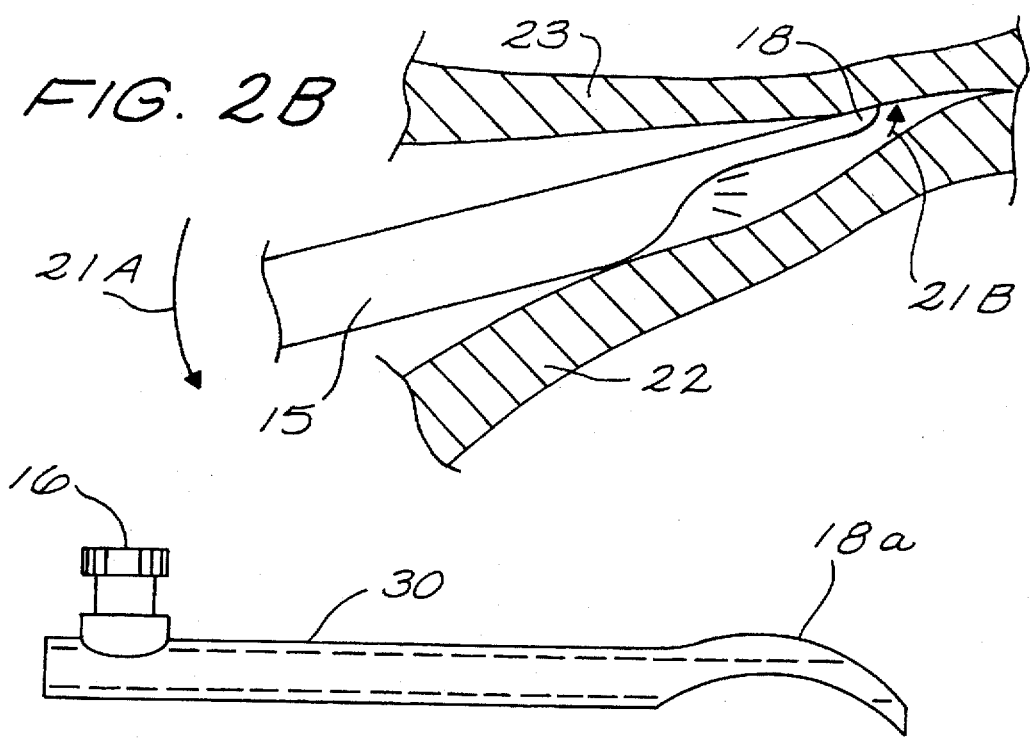
FIG. 2B
FIG. 1A
FIG. 1B
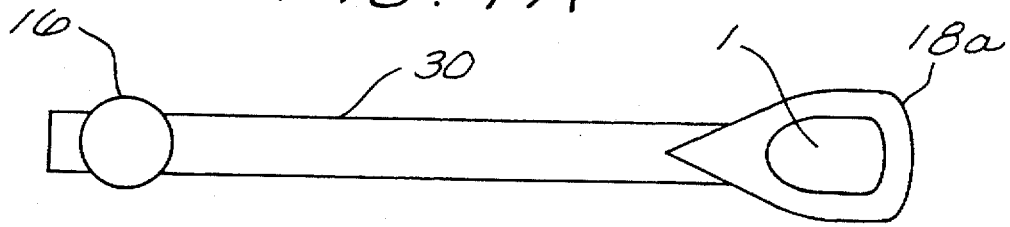
FIG. 3A
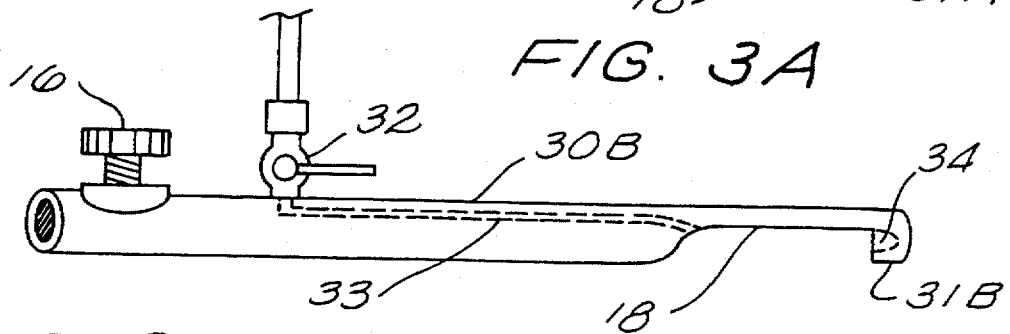
FIG. 3B

ENDOSCOPE AND TOOL THEREFORE

BACKGROUND

This is a continuation-in-part of United States patent application Ser. No. 08/318,196, filed Oct. 5, 1994, now abandoned and entitled "An Improved Endoscope and Tool Therefore."

This invention relates generally to surgical tools and, more particularly, to endoscopes and their attachments.

Endoscopy is credited as being first developed in the early 1900's. In general, endoscopy is the examination of a body cavity through the use of a tub-like instrument lenses and a light source.

In the 1930's, with the advance of optics and light sources, endoscopy began in earnest. A semiflexible gastroscope was probably the first truly viable endoscope and permitted surgical vision to extend into a heretofore impossible realm. With the advent of fiber optics, this range of application for the endoscope was enhanced and endoscopy came into its own.

In concept, the endoscope is a relatively simple device. The typical endoscope is a bundle of light-transmitting fibers having their emitting end in close proximity to a miniature telescope's viewing lens. The surgeon, peering through the telescope, is able to examine the body cavity with the assist of the light from the fibers. In this manner, tumors and disorders are located. It is this "hands on" vision that gives the surgeon such expanded capability.

If there is a cavity where the endoscope's lens is positioned, such as in the lungs, the endoscope is able to provide a good image for the surgeon. On the other hand, when the surgeon is exploring within tissue, the various tissues and organs press against the lens of the endoscope making it impossible to obtain a clear image and discern what is actually being viewed.

To remedy this problem, an inert gas such as nitrogen is sometimes injected into the area of interest to create an artificial cavity so that the endoscope can obtain proper visibility. Although this gas does increase the visibility significantly, it also subjects the tissues and organs of the patient to increased stress and damage and is much more invasive than desired.

Another problem with endoscope use is their complexity. Involved in the proper operation of the endoscope is its guidance and positioning, control of the water/wash for cleansing the lens, manipulation of any surgical tool associated with the endoscope (e.g. forceps, biopsy tool, scissors), manipulation of the light, and more.

Often it takes at least two surgeons working in unison to perform the many functions and operations required. This simultaneous coordination and cooperation of efforts between multiple surgeons is difficult at best. The different surgeons often are utilizing endoscopes which are equipped with a variety of surgical tools.

The tools which have been combined with the endoscope make it extremely complex for a single surgeon to properly manipulate. Examples of these surgical tools include: U.S. Pat. No. 4,060,086, entitled "Endoscope with an Operating Device," issued to Storz on Nov. 29, 1977; U.S. Pat. No. 4,973,321, entitled "Cannula for an Arthroscope," issued to Michelson on Nov. 27, 1990; U.S. Pat. No. 5,197,963, entitled "Electrosurgical Instrument with Extendable Sheath for Irrigation and Aspiration," issued to Parins on Mar. 30, 1993; U.S. Pat. No. 3,939,840, entitled "Operation Endoscope," issued to Storz on Feb. 24, 1976; U.S. Pat. No. 4,994,062, entitled "Resectoscope Apparatus," issued to Nishigaki et al. on Feb. 19, 1991; U.S. Pat. No. 4,499,899, entitled "Fiber-Optic Illuminated Microsurgical Scissors," issued to Lyons, III on Feb. 19, 1985; and, U.S. Pat. No. 4,362,160, entitled "Endoscopes," issued to Hiltebrandt on Dec. 7, 1982. These are all complex mechanical and optical devices; each of which requires exacting eye-hand coordination.

This complex physical manipulation required for these surgical instruments makes it difficult to conduct some operations and lengthens the time to perform others.

It is clear that improvements in the operation and capability of the endoscope will provide for improved medical attention and effectiveness. The following invention accomplishes these goals.

SUMMARY OF THE INVENTION

The invention creates an improved endoscope and tool therefore through the use of a shroud for the protection of the viewing end of an endoscope. The shroud helps maintain a distance between the lens and nearby tissue and organs.

The shroud is also used to separate tissue to improve the view through the endoscope. The surgeon, by prying the shroud between two body parts (e.g. muscle and bone), is able to create a microcavity in which vision of that area is possible.

The shroud is equipable with surgical tools to assist in the slicing, cauterizing, and biopsy removal. The improved endoscope and tool permit the surgeon to perform more activities while simultaneously reducing the need for an assisting surgeon. Additionally, the shroud is extremely useful in dissecting, moving, or relocating tissue during the surgical operation.

The shroud, in the preferred embodiment, provides two services:

(1) it protects the endoscope lens and permits the creation of micro-cavities for viewing purposes; and, (2) it serves as a platform on which surgical tools can be carried.

The shroud keeps tissue from pressing against the lens of the endoscope making for a clearer view of the area of interest. Unlike the current art which has the lens/tip as the penetrating point, the present invention uses the shroud as the penetrating point for the endoscope and the shroud shields the lens/tip of the endoscope from being pressed against tissue, bone, muscle, organs or other body parts and obscuring the endoscope's vision.

In this context, the preferred embodiment uses a shroud which extends in the range of a quarter of an inch to more than one inch in length past the lens/tip of the endoscope.

By "wedging" or "prying" the shroud between tissues, bone, or organs, the surgeon is able to create a micro-cavity for viewing. Just as a pencil is able to delicately separate sheets of paper in a stack, the shroud is also used to expose an area of the body without undue trauma to that locale.

Because the trauma to the body is minimized, the overall detrimental affect on the patient is also minimized providing for significantly reduced convalescence.

Additionally, the tip of the shroud is ideal for the incorporation of a surgical tool such as: a blade for cutting of flesh or chipping of bone; a dissector; a cauterizing point; a tubing for evacuating smoke, blood, or other matter; or a biopsy retrieval cup. In each of these cases, the surgical tool at the tip of the shroud is accurately positioned to be easily viewed through the endoscope.

The shroud is an extension of a cannula and is easily attached to the endoscope. In this context, a cannula is either; a slidably mounted "tube-like" apparatus that affixes to the endoscope's tube; or otherwise fastens to the endoscope tube using a mechanism such as a dip or other mechanism well known to those of ordinary skill in the art. The cannula, in the preferred embodiment, totally encircles the endoscope's tube; but, other embodiments use a cannula which only partially encircles the endoscope's tube.

Because the preferred embodiment of the present invention involves an external cannula which is slidably mounted to the endoscope, the cannula and its attendant surgical tool is easily and quickly changed to meet the demands of the surgeon.

Additionally, the external cannula with shroud, being removably from the endoscope, may be sterilized using techniques which would be harmful to the endoscope. This greatly enhances and simplifies the sterilization process.

In this application, a surgeon, with this improved endoscope combination, is able to easily view a location and then scrape, biopsy, or cut while maintaining vision of the site.

DRAWINGS IN SUMMARY

FIG. 1 is a side view of an endoscope employing the preferred embodiment of the present invention.

FIG. 1A is a side elevation view of an alternative embodiment of the invention which employs a curved shroud section.

FIG. 1B is a top elevation view of an alternative embodiment of the invention which employs a curved shroud section.

FIGS. 2A and 2B illustrate a surgeon using the preferred embodiment and the invention's use to create micro-cavities for viewing ease.

FIGS. 3A, 3B, 3C, 3D, 3E, and 3F show alternative embodiments of the preferred invention and its alternatives employing various surgical tools on the cannula.

Figure 4A:
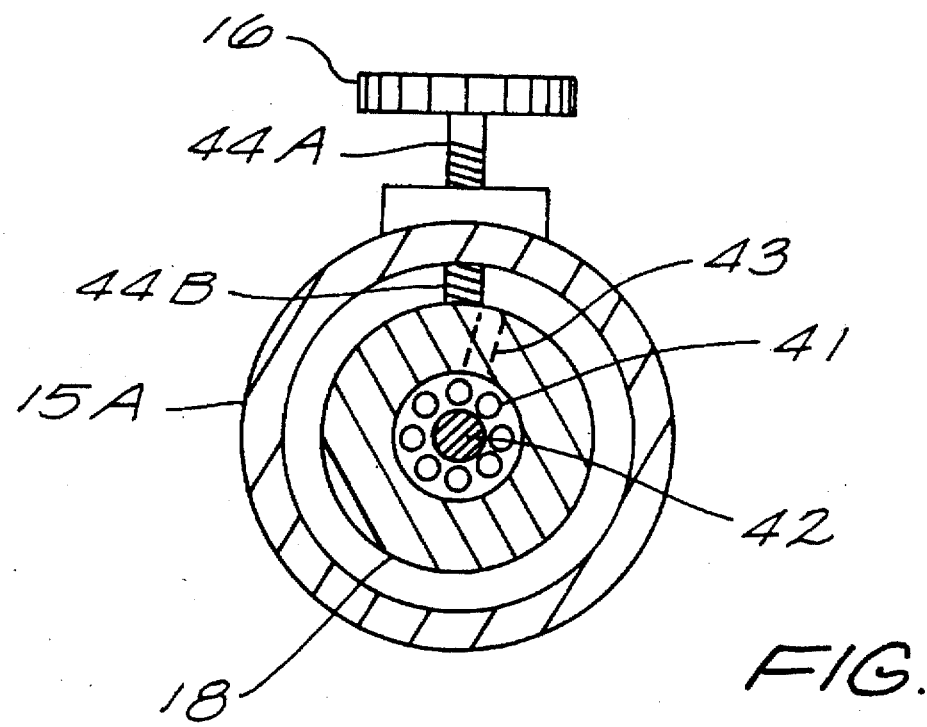
Figure 4B:
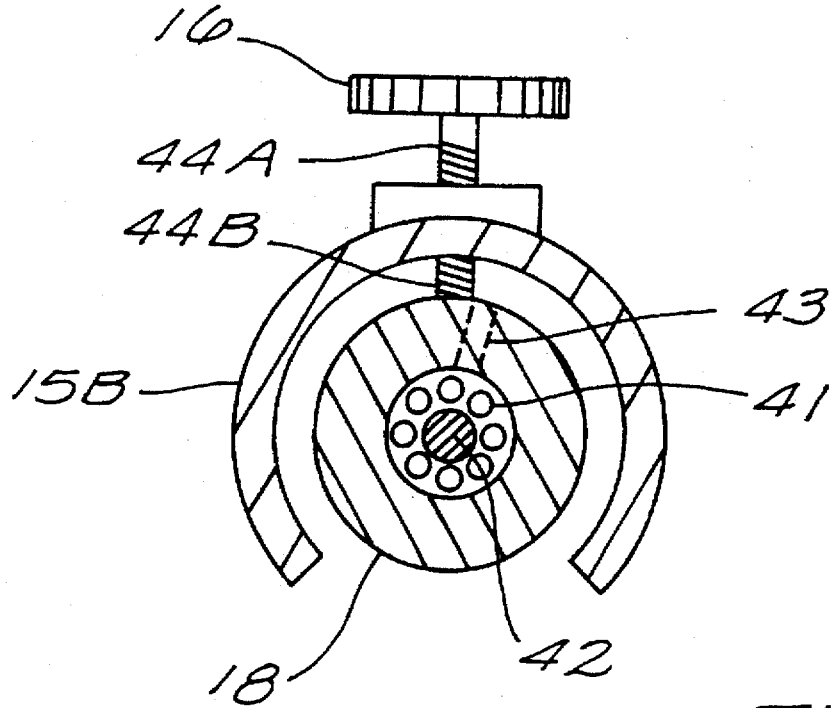

FIGS. 4A and 4B are frontal views of two embodiments of the invention showing the securement of the cannula to the endoscope.

DRAWINGS IN DETAIL

FIG. 1 is a side view of an endoscope employing the preferred embodiment of the present invention.

Using viewer 10A, the surgeon views through tube/cannula 10B and then through tip 10C to see inside the patient (not shown). Light, from light cable 11, is transmitted along the same cannula 10B to exit at tip 10C to illuminate the locale of interest. To keep the lens on tip 10C clean for viewing, water tubing 14 provides a wash of the tip 10C.

Handles 12A and 12B are utilized by the surgeon to manipulate various devices which are being viewed by the endoscope 19.

Outer cannula 15 surrounds cannula 10B and is secured thereto by attachment means 16, a screw lock mechanism in this embodiment. Shroud 18 extends past tip 10C and provides a protection and tool for endoscope's 19 operation. As noted earlier, the shroud's extension is at least a quarter of an inch and can extend for over an inch in length, depending on the needs of the surgeon.

Wash line 17 is also used by outer cannula 15 to provide a washing action between cannula 10B and outer cannula 15, exiting around tip 10C and washing over shroud 18.

FIG. 2A illustrates a surgeon using the preferred embodiment.

As shown, surgeon 20 peers through viewer 10A for a clear view of the interior of a patient. Note that surgeon 20 is able to physically manipulate the endoscope to vary its angle and positioning within the patient (not shown).

This manipulation, as shown in FIG. 2B, permits the surgeon to position cannula 15 and shroud 18 between two layers of tissue and organs, as illustrated by 22 and 23. Movement 21A causes a complimentary action 21B moving shroud 18 to separate tissue 22 from tissue 23 and thereby creating a micro-cavity for viewing through the endoscope.

In this manner, the surgeon is able to pry apart or dissect tissues and obtain a clear view between the tissues without having to inject any gas to create a cavity. Since the cavity formed by the shroud is so small in size, the detrimental effect on the tissues and organs of the patient is negligible, allowing the patient to quickly recover without a long convalescence.

While FIG. 1 shows the preferred embodiment of shroud 18 extending substantially straight past tip 10C, FIG. 1A shows an alternative embodiment. With reference to both FIG. 1 as well as FIGS. 1A and 1B, in this embodiment of the outer cannula, the shroud is curvilinear in shape and extends about tip 10C. In this embodiment, shroud 18a is curved and blended into the outer lines of cannula 15. This prevents traumatization of tissue when the apparatus is in use. Traumatization is further reduced in this embodiment through the curvilinear structure of shroud 18a. Specifically, unlike the preferred embodiment, the alternative embodiment's curved structure enables shroud 18a to "guide" tissue over its outer surface as opposed to "pushing" shroud 18a through tissue and forcing the tissue to separate.

Further, the view of surgeon 20 (FIG. 2A) through viewer 10a and tip 10c remains unobstructed even though shroud 18a curves around the front of tip 10c. This is so because shroud 18a has opening 1 as depicted in FIG. 1B which is a top view of the alternative embodiment shown in FIG. 1A. Through opening 1, tip 10c provides surgeon 20 (FIG. 2A) with a clear view of anything ahead of shroud 18a.

Figure 3C:
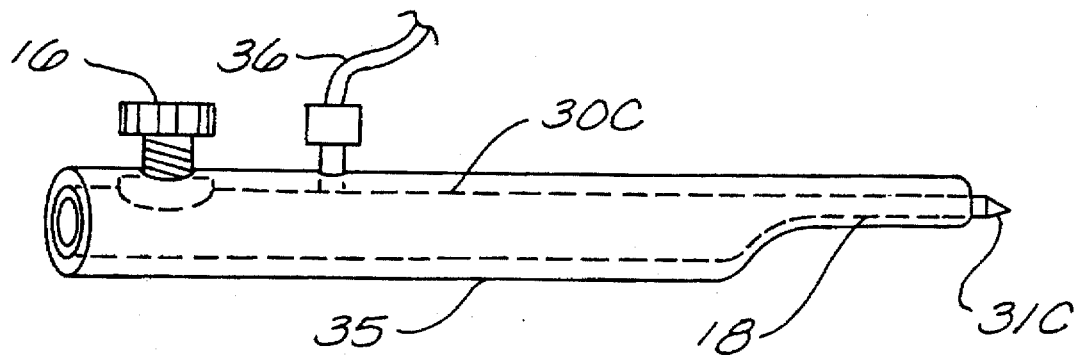

FIGS. 3A, 3B, and 3C show alternative embodiments of the invention which employ various surgical tools on the cannula. By providing surgical tools on shroud 18, the surgeon's range of skills is expanded without increasing the number of "hands" involved in the surgery.

As shown in FIG. 3A, outer cannula 30A is secured by fastening means 16. In this embodiment, a screw attachment is used, but those of ordinary skill in the art readily recognize various other mechanisms which will secure the outer cannula to the endoscope such as U.S. Pat. No. 5,087,080, entitled "Arthroscopic Sheath with Quick Coupling Socket" issued to Shutt on Feb. 11, 1992, and incorporated hereinto by reference.

In this embodiment, shroud 18 is equipped with surgical blade 31A which permits the surgeon to view an item through the endoscope and then to cut the tissue, bone, or other body parts while maintaining the action in sight. This permits a more defined and skilled use of the surgical blade.

In FIG. 3B, outer cannula 30B is secured by fastening means 16. Shroud 18 is equipped with a biopsy gathering tool 31B which has a cavity 34 therein. By pushing shroud 18 and biopsy tool 31B over an area of interest, then by withdrawing the endoscope, the tissue is scooped into cavity 34. This allows the surgeon to easily gather biopsy samples.

Should an incorrect sample be gathered, wash is communicated from valve 32 through channel 33 to the shroud 18. Channel 33 is directed toward cavity 34, thereby allowing the surgeon to wash cavity 34 and remove an unwanted biopsy sample. This in-situ washing eliminates the need to withdraw the endoscope to cleanse the biopsy tool 31B for reinsertion to obtain the desired sample.

The same channel 33 is also used to cleanse other surgical tools during operation. As example, should the surgical blade become blunted by bone fragment, the wash is able to remove the bone fragment with extreme ease.

Still further, another use of the channel is for the evacuation of smoke, blood, and other debris from the surgical site. In this context, valve 32 is used to selectively control the suction or vacuum being applied to tube 33 which carries the materials from the site close to the endoscope tube.

This particular aspect is especially useful when combined with the scalpel described relative to FIG. 3A in that, as bone and tissue are dislodged, they are easily and expeditiously removed from the surgical site using only a single instrument.

In the same way, smoke caused through either laser or electrical cauterization is also removed from the site so that a clear image is maintained.

FIG. 3C illustrates the use of outer cannula 30C, secured by fastening means 16, which has been coated with insulating material 35. An electrical current is created through connector 36 and exposed tip 31c. With electrical connection to the patient (not shown), the surgeon can selectively cauterize within the patient.

In this embodiment, shroud 18, and specifically tip 31c, is positioned to contact the targeted area and then electrical current is induced through tip 31c to cauterize. Note that all of this is done while being viewed through the endoscope, not shown, contained within the outer cannula 30c.

Those of ordinary skill in the art readily recognize various other cauterizing techniques which can be employed in this context including: U.S. Pat. No. 5,176,677, entitled "Endoscopic Ultrasonic Rotary Electro-Cauterizing Aspirator" issued to Wuchinich on Jan. 5, 1993; and, U.S. Pat. No. 5,195,958, entitled "Tool for Laparoscopic Surgery" issued to Phillips on Mar. 23, 1993.

In another application, the cauterizing mechanism is a laser which communicated to the tip of the shroud using fiber optics or the like. The laser is useful for either cauterizing or cutting tissue.

Figure 3D:
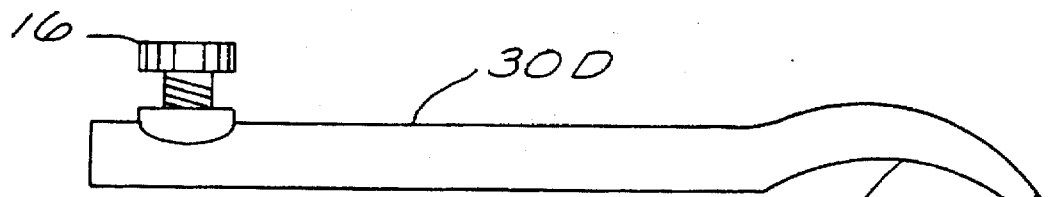

As shown in FIG. 3D, outer cannula 30D is secured by fastening means 16. In this embodiment, curvilinear shroud 18a of FIG. 1A similarly equipped with surgical blade 31A. In this embodiment, surgical blade 31A may consist of a separate structure or, alternatively, the leading edge of shroud 18a may be beveled so as to provide an effective cutting surface. In either case, this embodiment provides the apparatus with the benefits of having a curved shroud without eliminating any of the cutting capabilities provided for in the embodiment of FIG. 1A.

Figure 3E:
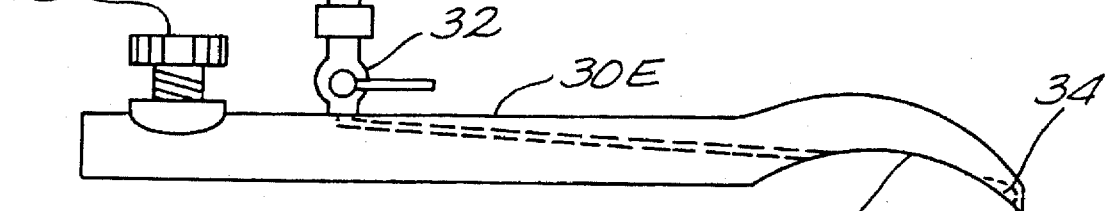

As shown in FIG. 3E, outer cannula 30E is secured by fastening means 16. In this embodiment, curvilinear shroud 18a as depicted in FIG. 1A is equipped with a biopsy gathering tool 31B and cavity 34 therein, as shown in the previous embodiment. Should an incorrect sample be gathered, wash is communicated from valve 32 through channel 33e to shroud 18a. The only difference between this embodiment and the embodiment of FIG. 3B is in the shape and configurement of shroud 18a. Therefore, all the benefits and added capabilities of having a curved shroud are provided for without sacrificing performance of the apparatus.

Figure 3F:
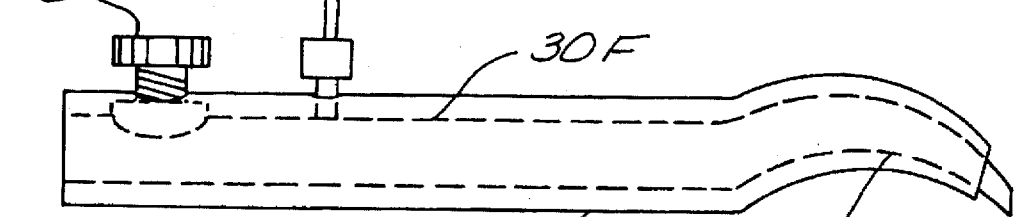

As shown in FIG. 3F, outer cannula 30F is secured by fastening means 16. Outer cannula 30f has been coated with insulating material 35. An electrical current is created through connector 36. In this embodiment, curvilinear shroud 18a as depicted in FIG. 1A has similar cauterizing capabilities as the embodiment illustrated in FIG. 3C. The only difference between this embodiment and the embodiment of FIG. 3C is in the shape of shroud 18a. Therefore, all the benefits and added capabilities of having a curved shroud are provided for without sacrificing the cauterizing capabilities of the apparatus.

FIGS. 4A and 4B are frontal views of two embodiments of the invention showing the securement of the cannula to the endoscope.

As shown in FIG. 4A, outer cannula 15a is secured to the cannula of the endoscope 18 via locking screw 16 which presses screw point 44b against cannula 18 via force from screw 44a.

Endoscope cannula 18 has viewing port 42 and light fibers 41 therein. Exhaust port or channel 43 permits wash or water to be communicated from around the light fibers 41 to the cavity between the endoscope cannula 18 and the outer cannula 15a.

Note that in this embodiment, cannula 15a totally encircles the inner endoscope cannula 18.

The embodiment of FIG. 4B is identical to the embodiment of FIG. 4A with the exception that outer cannula 15B does not totally encircle the endoscope cannula 18. This embodiment is secured by the locking screw 16.

It is clear from the foregoing that the present invention creates a new and improved endoscopic tool and endoscope assembly.

What is claimed is:

1. A combination comprising:
   a) an endoscope having a first cannula and a viewing end thereon;
   b) a tool for attachment to said endoscope, said tool comprising:
      1) a second cannula for at least partially encircling said first cannula, said second cannula having a shroud portion which, when said tool is attached to said endoscope, extends past the viewing end of said endoscope, said shroud portion being curvilinear in shape and extending in front of said viewing end of said endoscope, said shroud portion further having a cut-away section to allow unobstructed viewing through said viewing end of said endoscope and shroud portion, said shroud portion for shielding said viewing end of said endoscope during use of said endoscope in a patient, said shroud portion being a smooth extension of and substantially in line with an outer surface of said second cannula, said shroud portion including a surgical tool attached thereto; and,
      2) retaining means for securing said second cannula in static relationship with said first cannula such that during use, no part of said endoscope extends past said shroud portion.

2. The combination according to claim 1 wherein said surgical tool includes a cutting means for cutting tissue.

3. The combination according to claim 1 wherein said surgical tool includes a means for cauterizing tissue.

4. The combination according to claim 3 wherein said means for cauterizing includes a means for selectively passing an electrical current through selected tissues.

5. The combination according to claim 1 wherein said second cannula encircles said first cannula and wherein said first cannula includes exhaust ports for communicating wash to an area between said first cannula and said second cannula.

6. The combination according to claim 1 wherein said surgical tool includes means for retrieving a biopsy sample from a patient, said means for retrieving being attached to an underside portion of a leading edge of said shroud portion of said second cannula.

7. The combination according to claim 6 further including means for selectively directing wash into a cavity between said first cannula and said second cannula.

8. The combination according to claim 7 further including channel means for directing wash against said surgical tool for cleansing said surgical tool.

9. The combination according to claim 8 further including evacuating means for providing a partial vacuum, and wherein said channel means further includes means for communicating said partial vacuum to said shroud portion of said tool.

10. An attachment for use with an endoscope having a cannula with a viewing tip thereon, said attachment comprising an outer cannula attachable to a cannula of an endoscope, said outer cannula creating a shroud curvilinear in shape and extending in front of a viewing tip portion of an endoscope, said shroud including a surgical instrument, said outer cannula further having an opening proximate to said shroud, said opening extending substantially an entire circumference of said outer cannula, said opening at least partially exposing a viewing tip of an endoscope and shroud, said attachment secured to said endoscope such that no part of said endoscope can be moved past said shroud.

11. The attachment according to claim 10 wherein said surgical instrument includes cutting means positioned on a leading edge of said shroud, said cutting means for cutting body parts.

12. The attachment according to claim 10 wherein said surgical instrument includes means for cauterizing tissue in a patient.

13. The attachment according to claim 12 wherein said means for cauterizing includes means for selectively passing an electrical current through selected tissues.

14. The attachment according to claim 10 wherein said surgical instrument includes means for retrieving a biopsy sample from a patient, said means for retrieving being installed at a leading edge of said shroud.

15. The attachment according to claim 14 wherein said outer cannula encircles the cannula of said endoscope.

16. The attachment according to claim 10 further including means for selectively directing wash into a cavity located between the cannula of said endoscope and said outer cannula.

17. The attachment according to claim 16 further including channel means for directing wash from said cavity to said surgical instrument, said wash for cleansing said surgical instrument.

18. The tool according to claim 17 further including evacuating means for providing a partial vacuum, and wherein said channel means further includes means for communicating said partial vacuum proximate to said shroud.

19. A surgical combination comprising:
a) an endoscope permitting viewing of an interior of a patient through a viewing tube; and,
b) a cannula secured to and at least partially encircling said viewing tube, said cannula having,
1) an input port for communicating a wash to an interior cavity between said endoscope and said cannula,
2) a shroud, being an upper section of said cannula with an opening extending a majority of a circumference of said cannula, said shroud extending past and curving in front of a tip portion of said endoscope at least a half of an inch, said shroud for shielding said tip portion of said endoscope during use of said endoscope in a patient, said shroud further having a cut-away section providing for viewing by said endoscope through said viewing tube and said shroud, said shroud including a surgical tool attached thereto, and;
3) an attachment mechanism for connecting said cannula to said endoscope.

20. The surgical combination according to claim 19 wherein said surgical tool includes cutting means for cutting tissue.

21. The surgical combination according to claim 19 wherein said surgical tool includes means for cauterizing vessels in said patient.

22. The surgical combination according to claim 21 wherein said means for cauterizing includes means for selectively passing an electrical current through selected vessels in said patient.

23. The surgical combination according to claim 19 wherein said surgical tool includes means for retrieving a biopsy sample from said patient.

24. The surgical combination according to claim 19 further including channel means for directing a wash against said surgical tool for cleaning said surgical tool.

25. The surgical combination according to claim 24 further including evacuating means for providing a partial vacuum, and wherein said channel means further includes means for communicating said partial vacuum proximate to said shroud.

26. A surgical tool comprising:
a) an endoscope permitting visual inspection of an interior of a patient via an endoscope cannula; and,
b) an outer cannula secured to said endoscope cannula and at least partially encircling said endoscope cannula, said outer cannula including a shroud having,
1) a curved extension portion extending past and in front of a viewing end of said endoscope cannula during use of said endoscope in a patient,
2) an opening extending the length of said shroud, said opening being positioned to include at least a majority of a circumference of said outer cannula and permitting viewing by said endscope through said shroud, and,
3) a surgical tool attached to said shroud.

27. The surgical tool according to claim 26 wherein said surgical tool includes cutting means for slicing tissue.

28. The surgical tool according to claim 26 wherein said surgical tool includes means for cauterizing vessels in a patient.

29. The surgical tool according to claim 28 wherein said means for cauterizing includes means for selectively passing an electrical current through selected vessels.

30. The surgical tool according to claim 26 wherein said surgical tool includes means for retrieving a biopsy sample from the patient.

31. The surgical tool according to claim 26 wherein said outer cannula encircles said endoscope cannula and wherein said endoscope cannula includes exhaust ports for the communication of a wash to an area between said endoscope cannula and said outer cannula.

32. The surgical tool according to claim 31 further including means for selectively directing wash into a cavity between said endoscope cannula and said outer cannula.

33. The surgical tool according to claim 32 further including channel means for directing a wash against said surgical tool for cleansing said surgical tool.

34. The surgical tool according to claim 33 further including evacuating means for providing a partial vacuum, and wherein said channel means further includes means for communicating said partial vacuum proximate to said shroud.

* * * * *